(12) United States Patent
Zien et al.

(10) Patent No.: US 10,672,514 B2
(45) Date of Patent: Jun. 2, 2020

(54) SYSTEMS AND METHODS FOR CLINICAL DECISION SUPPORT

(71) Applicant: Molecular Health GmbH, Heidelberg (DE)

(72) Inventors: Alexander Zien, Heidelberg (DE); David B. Jackson, Heidelberg (DE); Martin Stein, Mannheim (DE); Guillaume Taglang, Heidelberg (DE); Stephan Brock, Weinheim (DE); Alexander Picker, Heidelberg (DE); Theodoros Soldatos, Heidelberg (DE); Bernhard Sulzer, Heidelberg (DE)

(73) Assignee: Molecular Health GmbH, Heidelberg (DE)

(*) Notice: Subject to any disclaimer, the term of this patent is extended or adjusted under 35 U.S.C. 154(b) by 1101 days.

(21) Appl. No.: 14/763,027

(22) PCT Filed: Oct. 1, 2013

(86) PCT No.: PCT/EP2013/070493
§ 371 (c)(1),
(2) Date: Jul. 23, 2015

(87) PCT Pub. No.: WO2014/117875
PCT Pub. Date: Aug. 7, 2014

(65) Prior Publication Data
US 2015/0370982 A1     Dec. 24, 2015

Related U.S. Application Data

(63) Continuation-in-part of application No. PCT/EP2013/056963, filed on Apr. 2, 2013, and a
(Continued)

(51) Int. Cl.
*G16H 50/20*     (2018.01)
*G16H 10/20*     (2018.01)
(Continued)

(52) U.S. Cl.
CPC ............. *G16H 50/20* (2018.01); *G16H 10/20* (2018.01); *G16H 50/30* (2018.01); *G16H 50/70* (2018.01)

(58) Field of Classification Search
CPC ................................ G16H 50/30; G16H 50/20
See application file for complete search history.

(56) References Cited

U.S. PATENT DOCUMENTS

2006/0062859 A1* 3/2006 Blum ..................... A61K 31/56
                                                                  424/725
2008/0311563 A1  12/2008 Mrazek et al.
(Continued)

FOREIGN PATENT DOCUMENTS

EP          1 176 539 A1    1/2002
JP          2002-510817      4/2002
(Continued)

OTHER PUBLICATIONS

Petricoin, Emanuel, "Mapping Molecular Networks Using Proteomics: A Vision for Patient-Tailored Combination Therapy," Journal of Clinical Oncology, Biology of Neoplasia, vol. 23, No. 15, May 20, 2005 (Year: 2005).*
(Continued)

*Primary Examiner* — John P Go
(74) *Attorney, Agent, or Firm* — Foley & Lardner LLP

(57) ABSTRACT

The present disclosure relates to systems and methods for bioinformatics and data processing. In particular, in a first aspect, the present disclosure relates to methods and systems for generating a personalized treatment guideline for a patient and for selecting a treatment for a patient. In another aspect, the present disclosure relates to methods and systems for selecting patients for a clinical trial of a treatment. The invention resolves cases in which patients have more than one "actionable" aberration by combining the patient-specific molecular information and the treatment-specific
(Continued)

molecular information further with a clinico-molecular disease model, specifically a scoring of genes and/or proteins that represents several aspects of their involvement into the disease. In this way, treatments and patients can be prioritized that are most likely to impact or impacted by the disease mechanism, respectively.

8 Claims, 4 Drawing Sheets

Related U.S. Application Data continuation-in-part of application No. PCT/EP2013/064621, filed on Jul. 10, 2013.

(60) Provisional application No. 61/757,805, filed on Jan. 29, 2013.

(51) Int. Cl.
  G16H 50/30 (2018.01)
  G16H 50/70 (2018.01)

(56) References Cited

U.S. PATENT DOCUMENTS

| | | | |
|---|---|---|---|
| 2010/0216660 A1 | 8/2010 | Nikolsky et al. | |
| 2012/0016594 A1 | 1/2012 | Christman et al. | |
| 2013/0316338 A1 | 11/2013 | Offner-Vandenbark et al. | |

FOREIGN PATENT DOCUMENTS

| | | | | |
|---|---|---|---|---|
| JP | 2002-539561 | | 11/2002 | |
| JP | 2003-242153 | A | 8/2003 | |
| JP | 2003-281156 | A | 10/2003 | |
| JP | 2004-130090 | | 4/2004 | |
| JP | 2004-517394 | | 6/2004 | |
| JP | 2006-323830 | A | 11/2006 | |
| JP | 2009-518040 | A | 5/2009 | |
| JP | 2012-123837 | | 6/2012 | |
| JP | 2012-196235 | A | 10/2012 | |
| WO | WO-99/52025 | A2 | 10/1999 | |
| WO | WO-02/37398 | A2 | 5/2002 | |
| WO | WO-03057916 | A2 * | 7/2003 | ........... C12Q 1/6886 |

OTHER PUBLICATIONS

Wu, Chia-Chin, "TARGETgene: A Tool for Identification of Potential Therapeutic Targets in Cancer," PLOS ONE, vol. 7, Issue 8, Aug. 2012 (Year: 2012).*
Wu, Chia-Chin, "TARGETgene: A Tool for Identification of Potential Therapeutic Targets in Cancer," PLOS ONE, Aug. 2012, vol. 7, Issue 8, e43305 (Year: 2012).*
Petricoin III, Emanuel F., "Mapping Molecular Networks Using Proteomics: A Vision for Patient-Tailored Combination Therapy," Jounral of Clinical Oncology, vol. 23, No. 15, May 20, 2005 (Year: 2005).*
"Genomics of Drug Sensitivity in Cancer: About", Wellcome Trust Sanger Institute, Feb. 28, 2013 (retrieved Oct. 23, 2015 from http://www.cancerrxgene.org/about/) 1 page.
Final Office Action for U.S. Appl. No. 13/828,862, dated Dec. 2, 2015.
Non-Final Office Action for U.S. Appl. No. 13/828,862, dated Dec. 20, 2017.
Chia-Chin Wu et al. "TARGETgene: A Tool for Identification of Potential Therapeutic Targets in Cancer", PLOS ONE, vol. 7, No. 8, p. e43305, Aug. 31, 2012.
D. Rebholz-Schuhmann et al: "EBIMed—text crunching to gather facts for proteins from Medline", Bioinformatics, vol. 23, No. 2, pp. e237-e244, Jan. 15, 2007.
International Search Report and Written Opinion dated Aug. 2, 2013 in PCT Application No. PCT/EP2013/056963.
International Search Report and Written Opinion dated Feb. 5, 2014 in PCT Application No. PCT/EP2013/070493.
International Search Report and Written Opinion dated Oct. 11, 2013 in PCT Application No. PCT/EP2013064621.
L. Tanabe et al: "MedMiner: An Internet Text-Mining Tool for Biomedical Information, with Application to Gene Expression Profiling", BioTechniques vol. 27, pp. 1210-1217, Jan. 1, 1999, URL: http://www.biotechniques.com/multimedia/archive/00007/99276bc03_7197a.pdf.
Oscar Krijgsman et al "A diagnostic gene profile for molecular subtyping of breast cancer associated with treatment response" Breast Cancer Research and Treatment, vol. 133, No. 1, pp. 37-47, Aug. 4, 2011.
Petricoin Emanuel F et al "Mapping molecular networks using proteomics: a vision for patient-tailored combination therapy" Journal of Clinical Oncology, vol. 23, No. 15, pp. 3614-3621, May 20, 2005.
Sophia Ananiadou et al. "Event extraction for systems biology by text mining the literature", Trends in Biotechnology, vol. 28, No. 7, pp. 381-390, Jul. 1, 2010.
Thomas C. Rindflesch et al: "EDGAR: Extraction of Drugs, Genes and Relations from the Biomedical Literature", Pac Symp Biocomput. pp. 517-528, Jan. 1, 2000, URL: http://www.ncbi.nlm.nih.gov/pmc/articles/PMC2709525/pdf/nihms58771.pdf.
U.S. Office Action in U.S. Appl. No. 13/828,862 dated Apr. 23, 2015.
Y. Tsuruoka et al: "FACTA: a text search engine for finding associated biomedical concepts", Bioinformatics, vol. 24, No. 21, pp. 2559-2560, Nov. 1, 2008.
U.S. Office Action on U.S. Appl. No. 14/763,015 dated Feb. 6, 2018.
Final Office Action on U.S. Appl. No. 13/828,862 dated Nov. 2, 2018.

* cited by examiner

SYSTEMS AND METHODS FOR CLINICAL DECISION SUPPORT

RELATED APPLICATIONS

The present application claims priority to and is a national phase entry of P.C.T. Application Ser. No. PCT/EP2013/070493, entitled "Systems and methods for clinical decision support," filed Oct. 1, 2013, which claims priority to P.C.T. Application Ser. No. PCT/EP2013/064621, filed Jul. 10, 2013; P.C.T. Application Ser. No. PCT/EP2013/056963, filed Apr. 2, 2013; and U.S. Provisional Application Ser. No. 61/757,805, filed Jan. 29, 2013, each of which are hereby incorporated by reference in their entirety.

FIELD OF THE DISCLOSURE

The present disclosure relates to systems and methods for bioinformatics and data processing. In particular, in a first aspect, the present disclosure relates to methods and systems for generating a personalized treatment guideline for a patient and for selecting a treatment for a patient. In another aspect, the present disclosure relates to methods and systems for selecting patients for a clinical trial of a treatment.

BACKGROUND OF THE DISCLOSURE

A large number of publications exist regarding human disease etiology and progression, discussing various molecular entities such as proteins, small molecules such as metabolites, nutrients, drugs, transporters, enzymes, pathways, and other information. Additionally, with revolutionary advances occurring in profiling technologies, the amount of new literature is constantly increasing. With such a large mass of data, it may be difficult for researchers to easily and quickly perform analyses and for clinicians to identify personalized patient treatment options. With such a large mass of data, it may also be difficult for researchers and clinicians to select patients for a clinical trial of a given treatment.

There exist attempts to combine knowledge about the mode of action of treatments, specifically the targets of targeted drugs, with the results of molecular profiling of a patient in order to select an appropriate treatment. In "Personalized Medicine in a Phase I Clinical Trials Program: the MD Anderson Cancer Center Initiative" by Tsimberidou, Apostolia-Maria, Nancy G Iskander, David S Hong, Jennifer J Wheler, Gerald S Falchook, Siqing Fu, Sarina Piha-Paul, et al. (Clinical Cancer Research: an Official Journal of the American Association for Cancer Research 18, no. 22 (Nov. 15, 2012): 6373-6383. doi:10.1158/1078-0432.CCR-12-1627), the authors test a small set of drug-target-genes for a pre-defined set of aberrations, specifically mutations. Treatments are selected that target a protein encoded by a gene with an aberration. However, their data shows that more than 7% of the patients had more than one "actionable" aberration. With more extensive profiling this percentage is expected to increase. In such cases, it is not clear, which protein/aberration should best be targeted by the treatment to be selected.

BRIEF SUMMARY OF THE DISCLOSURE

According to a first aspect of the invention, a method for generating a personalized treatment guideline for a patient comprises retrieving an identification of a disease indication of the patient. The method further comprises assigning an indication-specific score to each gene or protein of a first set of genes or proteins, the indication-specific score reflecting an evidence of the gene or protein being associated with the disease indication of the patient. The method further comprises retrieving a molecular profile of the patient, wherein the molecular profile is a set of molecular measurements indexed by a second set of genes or proteins, the second set of genes or proteins being equal to the first set of genes or proteins or being a subset of the first set of genes or proteins. The method further comprises inferring, from the molecular profile, for each gene or protein of the first set of genes or proteins a possibly empty set of aberrations. The method further comprises assigning a profile-specific score to each gene or protein of the first set of genes or proteins, the profile-specific score reflecting a degree of how much the function of the genes or proteins is altered by the aberrations. The method further comprises assigning a patient-specific score to each gene or protein of the first set of genes or proteins, the patient-specific score of each gene or protein being based on both its indication-specific score and its profile-specific score. The method further comprises retrieving a set of targeted treatments, together with associated target proteins and/or the corresponding genes, from a treatment database. The method further comprises assigning a score to each targeted treatment from the set of targeted treatments by aggregating the patient-specific scores at least over its associated target proteins and/or corresponding genes that are in the first set of genes or proteins. The method further comprises generating the personalized treatment guideline as an ordered list of the targeted treatments, wherein the order of the targeted treatments is determined by their score.

In comparison to existing methods for treatment selection and/or assignment of patients to trials, the approach outlined above has qualitative advantages. The invention also allows to prioritize the most important mutations in the mechanistically most important proteins, thus providing a new level of actionability beyond established biomarkers. In a patient where no previously described biomarker is found, this approach may be used to define the most likely actionable novel biomarker in the patient.

One advantage over the approach described by Tsimberidou et al. is that it provides a principled, bio-medically founded solution to the case of molecular aberrations being found in more than one gene or protein. This case is expected to be the standard case, once the profiling is performed to cover a large number of genes and/or proteins, which is desirable with respect to a comprehensive assessment and understanding of the patient and his/her disease. The method further comprises assigning a profile-specific score to each gene or protein of the first set of genes or proteins, the profile-specific score reflecting a degree of how much the function of the genes or proteins is altered as compared to a fixed reference state. Specifically, this score allows for going beyond a simple binary attribution of genes and/or proteins as either being mutated or not. In some embodiments, this invention further allows to match treatments to aberrations based on indirect, so-called downstream effects, hence providing treatment selection guidance even in cases in which no treatment directly targets a gene or protein with an aberration.

The invention thus resolves cases in which patients have more than one "actionable" aberration by combining the patient-specific molecular information and the treatment-specific molecular information further with a clinico-molecular disease model, specifically a scoring of genes and/or proteins that represents several aspects of their involvement into the disease. In this way, treatments can be prioritized that are most likely to impact the disease mechanism.

While much of this invention is described in the context of oncology, which is a preferred area of its application, it should be understood that the invention is of a general nature that extends to all kinds of diseases and conditions that have a molecular foundation (as opposed to, for instance, bone fractures, which are physical or mechanical in nature).

In embodiments of this invention that are directed towards treatment ranking or prioritization, an important choice is the selection of a set of treatments to be ranked. An obvious choice is to consider all treatments that are approved for the indication of the present patient. An alternative choice is to consider all treatments that are either approved or under development for that indication. In some application areas, for instance some rare cancers, there may not exist any approved treatments, or the set of existing approved treatments may already be exhausted for a given patient, meaning that these treatments have been tried unsuccessfully or that they are not applicable due to some counter-indication like an idiosyncrasy or a toxic interaction with another vital medication. Then it can be useful to consider treatments that are approved for a broader disease indication area, which is here defined as a set of related indications. Relatedness of indications may be judged according to a disease ontology, for instance MeSH or MedDRA. The necessary and sufficient degree of relatedness of indications may depend on the numbers of treatments available for related indications.

According to a first embodiment, the treatments are manually entered. According to another embodiment, the treatments are selected based on the disease indication of the patient or on a disease indication area of the patient.

The method may further comprise a step of outputting the personalized treatment guideline to a user as a list comprising one or more of the highest ordered targeted treatments, in particular by displaying them on a screen or display or by printing them onto paper.

According to a variant, a method for selecting a treatment for a patient comprises the steps: generating a personalized treatment guideline for the patient by executing the method steps as specified herein, and selecting the first targeted treatment from the ordered list of the targeted treatments of the personalized treatment guideline. The method may also comprise administering a selected treatment to the patient.

According to a second aspect of the invention, a method for selecting patients for a clinical trial of a treatment comprises retrieving identifications of disease indications of a set of patients. The method further comprises assigning, for every patient, an indication-specific score to each gene or protein of a first set of genes or proteins, the indication-specific score reflecting an evidence of the gene or protein being associated with the disease indication of the patient. The method further comprises retrieving, for every patient, a molecular profile of the patient, wherein the molecular profile is a set of molecular measurements indexed by a second set of genes or proteins, the second set of genes or proteins being equal to the first set of genes or proteins or being a subset of the first set of genes or proteins. The method further comprises inferring, from the molecular profile, for each gene or protein of the first set of genes or proteins a possibly empty set of aberrations. The method further comprises assigning, for every patient, a profile-specific score to each gene or protein of the first set of genes or proteins, the profile-specific score reflecting a degree of how much the function of the genes or proteins is altered by the aberrations. The method further comprises assigning, for every patient, a patient-specific score to each gene or protein of the first set of genes or proteins, the patient-specific score of each gene or protein being based on both its indication-specific score and its profile-specific score. The method further comprises retrieving, from a treatment database, for the treatment those of its associated target proteins and/or corresponding genes that are also in the first set of genes and proteins. The method further comprises assigning a score to every patient from the set of patients by aggregating the patient-specific scores at least over the associated target proteins and/or the corresponding genes, and generating an ordered list of the patients, wherein the order of the patients is determined by their score.

The inventive methods denoted by first and to second aspects only differ from their input. In the first method, a set of treatments is being related to a single patient, whereas in the second method, a set of patients is being related to a single treatment. The involved scores may be computed analogously in both cases.

The indication-specific score of any gene or protein is computed by first assigning numerical values to attributes that indicate degrees of potential relationship of the gene or protein to the disease indication and then aggregating the numerical values over the attributes, in particular by forming a weighted sum of the values or of any monotonic transformation of the values, such as logarithms or exponentials. The indication-specific score reflects the evidence of the gene or protein being associated with the disease indication of the patient.

The indication-specific score may be based on scores assigned to at least one of the following attributes labeled by a) to k).

a) The gene or protein is a drug target.

The attribute "drug target" may involve a-specific sub-scoring schema involving further attributes. The score for the attribute "drug target", also referred to as a drug target score in the following, may be a sum, a product, or any function of sub-scores for the involved attributes. A first relevant attribute may be the relation of the drug to the indication. If the gene or protein is a drug target for a drug used in the-specific indication, then the drug target score may be attributed a high value. If the gene or protein is a drug target in a related indication, then the drug target score may be attributed a medium value. If the gene or protein is a drug target in an unrelated indication, then the drug target score may be attributed a low value. A second relevant attribute may be the developmental stage of the drug, e.g. experimental or approved. A low drug target score is related to the experimental stage and a high drug target score is related to the approved stage. A third relevant attribute may be a total number of targeting drugs, the drug target score thus being a function of the total number of targeting drugs. A fourth relevant attribute may be if the drug acts directly or indirectly on its target, a direct acting being related with a higher drug target score than an indirect acting. A fifth relevant attribute may be related to trials, in particular the total number of trials and the phase of a trial.

b) The gene or protein is a biomarker or part of a biomarker.

Biomarkers are values that indicate diagnosis, prognosis, response to treatment, or other clinically relevant information and that can be directly measured or computed from measurement values. A gene or protein is said to be a biomarker if the measurement of a value directly related to that gene or protein, for instance its expression level or its sequence, is a biomarker. Analogously, a gene or protein is said to be part of a biomarker when a measurement value directly related to it is required for the computation of a biomarker that may also involve other values. Similarly to the drug target score, the biomarker score of a gene or protein may be formed by combining several sub-scores that relate to attributes of the biomarker. Specifically, there may be sub-scores that reflect: the level of validation of the biomarker; the strength of the biomarker, in other words the effect size associated with a change in the biomarker value; and the relationship between the indications that the biomarker is relevant for and the patient indication.

c) The gene or protein is disease-associated.

The attribute "disease-associated" may involve another specific sub-scoring schema involving further attributes. The score for the attribute "disease associated", also referred to as a disease associated score in the following, may be a sum, a product or any function of sub-scores for the involved attributes. A first attribute may be if the gene or protein is part of an Online Mendelian Inheritance in Man (OMIM). A second attribute may be if the gene or protein is part of a disease ontology. A third attribute may be if the gene or protein has a text data mining co-occurrence with the indication, a related disease indication or an unrelated indication. For all of these attributes, the sub-score may depend on whether the gene or protein is associated with the specific indication, a related disease indication or an unrelated indication. If the gene or protein is associated with the specific indication, then the disease associated score may be attributed a high value. If the gene or protein is associated with a related indication, then the disease associated score may be attributed a medium value. If the gene or protein is associated with an unrelated indication, then the disease associated score may be attributed a low value. A fourth attribute may involve text data mining (TDM) metrics and statistics. A fifth attribute may be a validity, e.g. cell line, animal or clinical study.

d) The gene or protein is an oncogene or a product of an oncogene, respectively.

The attribute "oncogene" is associated with a fixed numerical contribution to the indication-specific score.

e) The gene or protein is a tumor suppressor.

The attribute "tumor suppressor" is associated with a fixed numerical contribution to the indication-specific score.

f) The gene or protein has a cancer pathway association.

The attribute "cancer pathway association" may involve counting of memberships in pathways. A specific cancer pathway association may be the Vogelstein core cancer association.

g) The gene or protein is gene ontology annotated for cancer relevant processes.

The attribute "gene ontology annotated for cancer relevant processes" is associated with a fixed numerical contribution to the indication-specific score.

h) The gene or protein is part of a cancer-associated gene fusion.

The attribute "part of a cancer-associated gene fusion" is associated with a fixed numerical contribution to the indication-specific score.

i) The gene or protein has a tractable domain.

With regard to "tractable domains", their contribution to the indication-specific score may be high if there are one or more tractable domains known, medium if they potentially exist and low if there are none.

j) The gene or protein is embryonic lethal.

The attribute "embryonic lethal" is associated with a fixed numerical contribution to the indication-specific score.

k) The gene or protein is highly mutated in the specific indication.

The attribute "Indication specific mutation rate" is associated with a fixed numerical contribution to the indication-specific score.

It is useful to define the indication-specific score such that it assumes only non-negative values; this can be achieved by defining it as a weighted sum of non-negative attribute scores with non-negative weights.

According to an embodiment, the indication-specific score is based on scores assigned to at least one of the attributes labeled by a) to c), which are not specific for cancer.

According to an embodiment of the method, the patient-specific score is a sum or a weighted sum of its indication-specific score and its profile-specific score.

It is preferred, however, that the patient-specific score is a product of its indication-specific score and its profile-specific score.

According to an embodiment, the profile-specific score is set to zero if the gene or protein has no aberrations.

The profile-specific score may simply be set to 1 if the gene or protein has one or more aberrations or may involve more sophisticated scoring schemes with aberration-specific functional impact scores.

Aberration-specific functional impact scores (aFIS) are scores that quantify the presumed impact of an aberration of a given gene or protein onto its function. In some embodiments, this score is signed (that is, it may assume negative values), such that the sign indicates the directionality of the impact, with a positive sign indicating an enhancing or activating effect, and a negative sign indicating an inhibitory or deactivating effect. In preferred embodiments, this score is normalized, such that a value of +1 would indicate permanent activation, and −1 would indicate complete deactivation of the function.

According to an embodiment, assigning a profile-specific score to each gene or protein of the first set of genes or proteins comprises computing an aberration-specific functional impact score for each aberration and computing a protein- or gene-specific direct functional impact score for each protein or gene by aggregating the aberration-specific functional impact score over the aberrations associated with the gene or protein.

Alternatively or additionally, assigning a profile-specific score to each gene or protein of the first set of genes or proteins comprises computing an aberration-specific functional impact score for each aberration and computing a protein- or gene-specific indirect functional impact score for each protein or gene by aggregating the aberration-specific functional impact score over the aberrations associated with a set of second genes or proteins, the set including the first gene or protein and a set of genes or proteins that are upstream of the first gene or protein according to a molecular interaction network.

These embodiments that consider effects of aberrations and/or treatments on genes or proteins downstream of the gene or protein that has the aberration or is a target of the treatment, respectively, enable to identify treatments that cannot be found by the direct matching of treatment targets to aberrations.

The profile-specific score may be set equal to the direct functional impact score, equal to the indirect functional impact score or equal to a weighted sum of these.

In some embodiments, the aberration-specific functional impact score also comprises an indication of the direction of the impact of an aberration on the function of a gene or protein, wherein positive and negative signs of the aberration-specific functional impact score correspond to an activating and inactivating impact, respectively.

Aggregating the aberration-specific functional impact scores over the aberrations may be formed by computing a weighted sum of all aberration-specific functional impact scores, in particular the plain sum of all functional impact scores or the mean of all functional impact scores. Alternatively, the aggregate of the aberration-specific functional impact scores may be formed as a weighted sum of all aberration-specific functional impact scores. Alternatively, aggregating the aberration-specific functional impact score over the aberrations may be formed by taking a quantile of all aberration-specific functional impact scores, in particular the median of all aberration-specific functional impact scores or the maximum of all aberration-specific functional impact scores. Alternatively, aggregating the aberration-specific functional impact score over the aberrations may be formed as the (possibly weighted) geometric mean of all aberration-specific functional impact scores.

If the aberration-specific functional impact scores represent probabilities of each of the aberrations impacting the function of the gene or protein, alternatively, aggregating the aberration-specific functional impact score over the aberrations may be performed by estimating the probability of the union of all aberrations impacting the function of the gene or protein, which can be implemented using the well-known inclusion-exclusion principle from combinatorics, in particular based on an assumption of mutual independence of the functional impact of the aberrations.

According to an embodiment, the aggregation of aberration-specific functional impact scores takes into account an indication of the direction of the impact of an aberration on the function of a gene or protein, wherein positive and negative signs of the aberration-specific functional impact score correspond to an activating and inactivating impact, respectively.

According to an embodiment, assigning a score to a treatment further takes into account a directionality of the impact of the treatment on its targets in aggregating over them by adding profile-specific scores of targets that are inhibited or antagonized by the treatment and subtracting profile-specific scores of targets that are activated or stimulated or agonized by the treatment.

According to an embodiment, assigning a score to each treatment is extended such that patient-specific scores are further aggregated over genes and/or proteins downstream of its targets according to a molecular interaction network.

In some embodiments, this invention takes advantage of an interaction network of proteins and/or genes. Such networks are frequently represented as graphs, consisting of nodes each of which represents a gene or a protein, and of edges each of which connects two nodes. In a directed network, edges have directions, pointing from a source node to a sink node. The source is said to be "upstream" of the sink; the sink is said to be "downstream" of the source. The relationships "upstream" and "downstream" are extended transitively: if, for instance, node A is upstream of node B and B is upstream of node C, then A is upstream of C and C is downstream of A. A directed path from one node X to another node Y is a sequence of nodes starting with X and ending with Y such that for each pair of successive nodes in the sequence there exists a directed edge from the first node in the pair to the second node in the pair.

In preferred embodiment, the molecular interaction network shall be represented by a directed graph with optional binary edge annotations, the annotations labeling an edge as either activating or inhibitory. An activating edge indicates that an increase in activity of the protein or gene represented by the source node triggers an increase in activity of the protein or gene represented by the sink node; analogously with decrease of activity. An inhibitory edge indicates that an increase in activity of the protein or gene represented by the source node triggers a decrease in activity of the protein or gene represented by the sink node; and vice versa.

Specifically, in some embodiments, the profile-specific score of a gene or protein is computed by aggregating aberration-specific functional impact scores (aFIS) in a way that takes into account the direction of the impact of an aberration onto the function of that gene or protein. Let X denote the gene or protein for which the profile-specific score shall be computed, then the aggregation is formed as a weighted sum of aFIS of aberrations of X and genes or proteins upstream of X. For any aberration of X itself, the weight is +1. For any aberration of a protein U upstream of X, the weight depends on the number of inhibitory edges in the considered path from U to X: the weight is −1 for odd numbers, and +1 for even numbers. This way, the directionality of the effect of U on X is reflected. In general there may exist more than one directed path from a node U to another node X; a preferred way of dealing with this is to only consider shortest paths, and to only consider upstream nodes U that have a single (unambiguous) shortest path.

According to the invention, a system for generating a personalized treatment guideline for a patient and/or for selecting patients for a clinical trial of a treatment comprises a processing unit with an interface for providing a first set of genes or proteins to the system. The system further comprises an interface for providing identifications of disease indications of patients to the system. The system further comprises a module for assigning, for an identification of a disease indication of a patient, an indication-specific score to each gene or protein of the first set of genes or proteins, the indication-specific score reflecting an evidence of the gene or protein being associated with the disease indication of the patient. The system further comprises an interface for providing molecular profiles of patients to the system, wherein a molecular profile is a set of molecular measurements indexed by a second set of genes or proteins, the second set of genes or proteins being equal to the first set of genes or proteins or being a subset of the first set of genes or proteins. The system further comprises a module for assigning, for a molecular profile of a patient, a profile-specific score to each gene or protein of the first set of genes or proteins. The module for assigning the profile-specific score is adapted to inferring, from a molecular profile, for each gene or protein of the first set of genes or proteins a possibly empty set of aberrations. The system further comprises a module for assigning a patient-specific score to each gene or protein of the first set of genes or proteins, the patient-specific score of each gene or protein being based on both its indication-specific score and its profile-specific score. The system comprises an interface for providing targeted treatments, together with associated target proteins and/or the corresponding genes, from a treatment database to the system, wherein the associated target proteins and/or the corresponding genes are another subset of the first set of genes or proteins. The system further comprises a module for assigning a score to patients and to treatments by aggregating the patient-specific scores at least over the associated target proteins and/or the corresponding genes. The module for assigning the score to patients and to treatments is adapted to generating ordered lists of patients or treatments, wherein the order of the patients or treatments is determined by their score.

In an embodiment, the module for assigning the profile-specific score is further adapted to assigning an aberration-specific functional impact score for each aberration and to aggregating the functional impact score over the aberrations if there are two or more aberrations in the gene or protein and assigning zero to the gene or protein if the gene or protein has no aberrations.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

Figure 1:
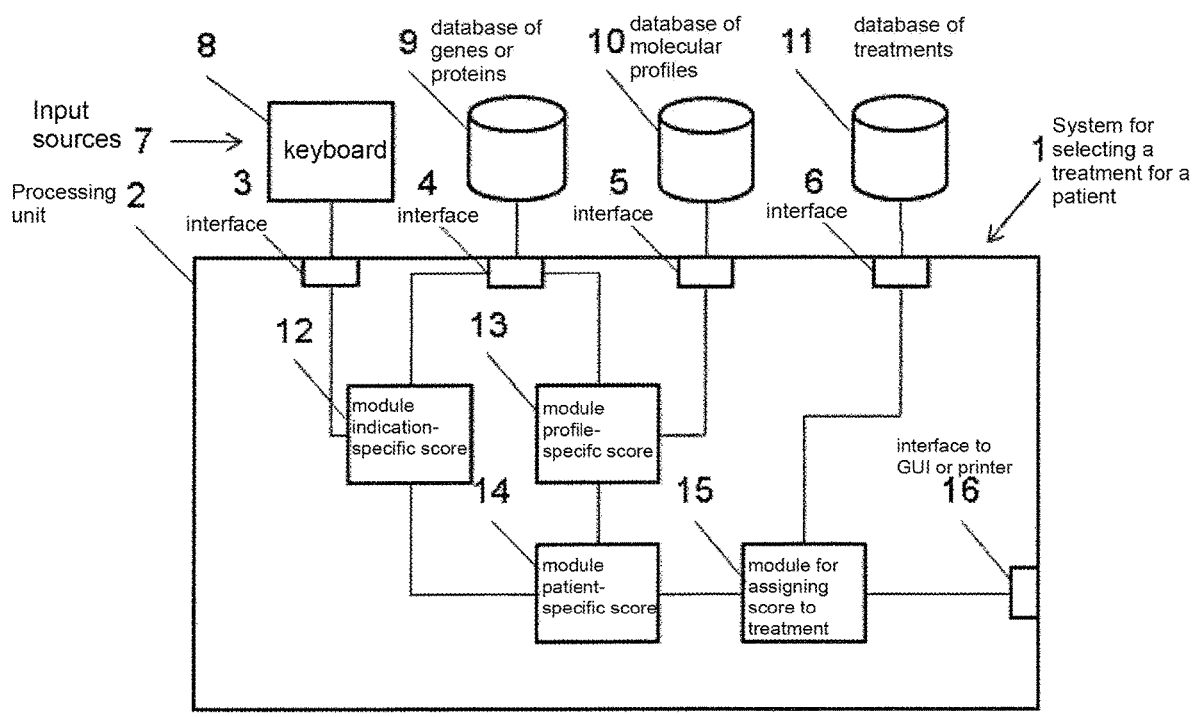
FIG. 1 is a block diagram of a system for generating a personalized treatment guideline for a patient or for selecting patients for a clinical trial of a treatment according to one implementation.

Prior to discussing specifics of methods and systems utilizing prioritization of patient treatment options, it may be helpful to briefly define a few terms as used herein. These definitions are not intended to limit the use of the terms, but rather may provide additional or alternate definitions for use of the terms within some contexts.

The term "aberration" refers to differences of a specific instance of a gene or protein to a reference version of that gene or protein. In the context of this invention, the specific instances of interest are those found in a given patient. The reference version is intended to represent what is "normal", i.e. what corresponds to a healthy state, typically with respect to humans in general, a specific human population or cohort, or the given patient. As an example, the reference state may be defined by what is found in a control tissue sample of the patient, whereas the aberrations are looked for in a tumor sample. As another example, the reference state may be defined as what is frequently found in a representative sample of humans. The difference that constitutes an aberration may be with respect to any biochemically or medically relevant property of the gene or protein. Examples include the sequence of a gene or protein, the structure of a protein, the DNA methylation status of a gene, the expression of a gene or protein, and post-translational modifications of a protein. A typical aberration in an ontology context is a somatic mutation, i.e. a sequence alteration in the tumor as compared to the germline The term "identification of a disease indication" is understood according to a disease ontology, eg MeSH, MedDRA, ICD-9, etc. For certain classes of indications there may also be specialized ontologies that may offer advantages like more precise categorization of the indication. For example, in oncology it may be beneficial to use ICD-O-3 and/or the TNM staging system.

The term "molecular profile" denotes a set of measurements indexed by a set of genes. The set of measurements is thus formed by measurements, wherein each measurement is associated with a gene of the human genome or a protein of the human proteome. The human genome and proteome are meant to include the genomes and proteomes of human symbionts, like gut bacteria. Examples of molecular profiles include the sequences of genes or, equivalently, the sets of sequence variants. Examples of molecular profiles further include the expression levels of genes and the expression levels of proteins. They can be measured by standard technology, including next generation sequencing (NGS) or microarrays. The measurement values are stored in a database or in files, from where they can easily be retrieved.

The term "set of genes or proteins" may generally denote a set of genes, a set of proteins, or a mixed set of genes and proteins.

A "weighted sum" of n summands $S_1, \ldots S_n$ may be any sum of the type $$S = \sum_{i=1}^{n} c_i \cdot S_i,$$

wherein $c_i$ are defined real numbers. The weights $c_i$ may be defined with further constraints, that they must be positive and/or that they must lay in a certain range of values.

FIG. 1 shows a system 1 for selecting a treatment for a patient or for selecting patients for a clinical trial of a treatment according to one exemplary implementation. The system 1 comprises a processing unit 2 equipped with interfaces 3, 4, 5, 6 for retrieving data from input sources 7. The retrieved data comprises identifications of disease indications of patients, sets of genes or proteins, molecular profiles of patients and targeted treatments, together with associated target proteins and/or the corresponding genes.

Processing unit 2 may operate in at least two operation modes. In a first mode, the input is an identification of a disease indication of a patient and several candidate targeted treatments. The processing unit 2 then generates a personalized treatment guideline for the patient. In a second mode, the input is identifications of a disease indication of several patients and one targeted treatment. The processing unit 2 then generates an ordered list of patients, providing a hint on their suitability for a clinical trial. The processing unit 2 may comprise a switch (not depicted), in particular a software switch for switching between the two operation modes. The switch may control an input mask, limiting a user's input in one or the other direction, or may control the amount of information retrieved from one or more databases, for instance by detailing an SQL query.

Interface 3 is adapted to providing an identification of a patient disease indication to the processing unit 2. The identification of a patient disease indication may be retrieved via a user, e. g. may be typed on a keyboard 8 or may be deduced from a free text typed on a keyboard 8, or selected from a multiple-choice element in a GUI (graphical user interface, not depicted). The patient disease indication may also be retrieved directly from an electronic health record (EHR) or electronic medical record (EMR), possibly on a chip-card or in a database (not depicted). The identification of a patient disease indication may also be retrieved from a patient database comprising medical records of a candidate set of patients (not depicted).

Interface 4 is adapted to providing a first set genes or proteins to the processing unit 2. The corresponding input source 7 consists of a database 9 of genes or proteins, which are part of the human genome or proteome in a broad sense, i.e. possibly including the genomes and proteomes of human symbionts or parasites, in particular the human microbiome. The database 9 further comprises a number of attributes of the genes or proteins which may be provided to the processing unit 2 via interface 4. Such attributes may include whether the gene or protein is a drug target, whether the gene or protein is a biomarker, whether the gene or protein is disease-associated, whether the gene or protein is an oncogene, whether the gene or protein is a tumor suppressor, whether the gene or protein has an association with a disease-relevant pathway (for instance, in a cancer pathway or in a Vogelstein core cancer pathway), whether the gene or protein is gene ontology annotated for disease-relevant processes, whether the gene or protein is part of a indication associated gene fusion, whether the gene or protein has a tractable domain, whether the gene or protein is embryonic lethal, whether the gene or protein is part of a Online Mendelian Inheritance in Man (OMIN), whether the gene or protein is part of a disease ontology, whether the gene or protein shows substantial co-occurrence with the specific indication, any related indication, or any indication at all, in a body of literature, as can be assessed by the use of text data mining and whether the gene or protein is found to be frequently mutated in that particular indication, using resources such as the COSMIC database. The database 9 may further hold information on normal or reference states of the proteins or genes, in particular the sequences of a reference genome (for instance, "hg19" or "GRCh37" by the Genome Reference Consortium) or "standard" versions of proteins (for instance, those stored in SwissProt) and/or commonly observed expression levels of genes or proteins (for instance, as stored in ArrayExpress or Gene Expression Omnibus).

Interface 5 is adapted to providing a molecular profile of the patient to the processing unit 2. Such molecular profiles may comprise measurements of DNA or RNA extracted from the patient, produced by molecular measurement technology, for instance NGS or microarrays. Molecular profiles may be stored in a database 10 or in a computer file (not shown), from which they are retrieved via interface 5.

Interface 6 is adapted to providing a set of targeted treatments, together with their associated target proteins and/or the corresponding genes, to the processing unit 2. A treatment may be provided by a user, e. g. may be typed on a keyboard or may be deduced from a free text typed on a keyboard, or selected from a multiple-choice element in a GUI (graphical user interface, not depicted). Interface 6 may then provide associated target proteins and/or the corresponding genes for the treatment from a treatment database 11. The treatment database 11 is a database that holds available treatments, in particular drugs and drug combinations, together with information on the proteins or genes that are the targets of the drugs. Alternatively, a set of targeted treatments, together with their associated target proteins and/or the corresponding genes, may directly be retrieved from a treatment database 11, without user's input. Specifically, treatments may be selected based on the disease indication of a patient, for instance by selecting treatments that are approved or under investigation for the indication of the patient or for related indications.

Processing unit 2 comprises a module 12 adapted to assigning an indication-specific score to genes or proteins, also referred to as module 12 for assigning the indication-specific score. The module 12 for assigning the indication-specific score retrieves data from interface 3 and interface 4. From database 9, a number of attributes of the genes or proteins are retrieved, the attributes indicating degrees of potential relationship to the indication. The indication-specific score of any gene or protein is computed by first assigning numerical values to the attributes and then aggregating the numerical values over the attributes, in particular by forming a weighted sum.

Processing unit 2 comprises another module 13 adapted to assigning a profile-specific score to genes or proteins, also referred to as module 13 for assigning the profile-specific score. The module 13 for assigning the profile-specific score retrieves data from interface 4 and interface 5. The module 13 for assigning the profile-specific score infers from the molecular profile for each gene or protein from a given molecular profile a possibly empty set of aberrations as compared to a reference. This reference may be provided by a second molecular profile, which corresponds to a reference state; an example of this is the common practice in oncology research to sequence both a tumor sample and a control sample, for instance, taken from blood. Alternatively, the reference may consist of measurements from other individuals that have been gathered before and from which typical measurement values of corresponding molecular profiles can be derived; such reference data may be stored with other gene- or protein-associated data in database 9.

The profile-specific score of any gene or protein is computed by assigning an aberration-specific functional impact score to each inferred aberration and aggregating the aberration-specific functional impact score over the aberrations associated with the gene or protein and/or associated with a set of second genes or proteins, the set including the first gene or protein and a set of genes or proteins that are upstream of the first gene or protein according to a molecular interaction network, if there are two or more aberrations in the gene or protein and assigning zero to the gene or protein if the gene or protein has no aberrations. Alternatively, the profile-specific score may be set to 1 if the gene or protein has one or more aberrations and set to zero if the gene or protein has no aberrations.

Processing unit 2 comprises another module 14 adapted to assigning a patient-specific score to genes or proteins, also referred to as module 14 for assigning a patient-specific score. The module 14 for assigning a patient-specific score retrieves data from the module 12 for assigning the indication-specific score and from the module 13 for assigning the profile-specific score. Module 14 is adapted to aggregating the indication-specific score and the profile-specific score. Preferably, the patient-specific score of every gene or protein is computed by multiplying the indication-specific score and the profile-specific score.

Processing unit 2 comprises another module 15 adapted to assigning a score to patients and treatments, also referred to as module 15 for assigning the score to patients and treatments. The module 15 for assigning the score to patients and treatments retrieves data from interface 6 and from module 14 for assigning the patient-specific score. Module 15 for assigning the score to patients and treatments is adapted to aggregating, for each targeted treatment, the patient-specific scores at least over its target proteins and/or the corresponding genes. The aggregation is performed by calculating a sum or a weighted sum over the patient-specific scores of the involved proteins and/or genes.

Module 15 for assigning the score to patients and treatments is further adapted to generating a personalized treatment guideline as an ordered list of the targeted treatments and to generating an ordered list of candidate patients for a clinical trial of a treatment. Module 15 for assigning the score to patients and treatments further makes personalized treatment guidelines or lists of candidate patients for a clinical trial of a treatment available to another interface 16 of the processing unit, which may by connected with a GUI or a printer.

Figure 2:
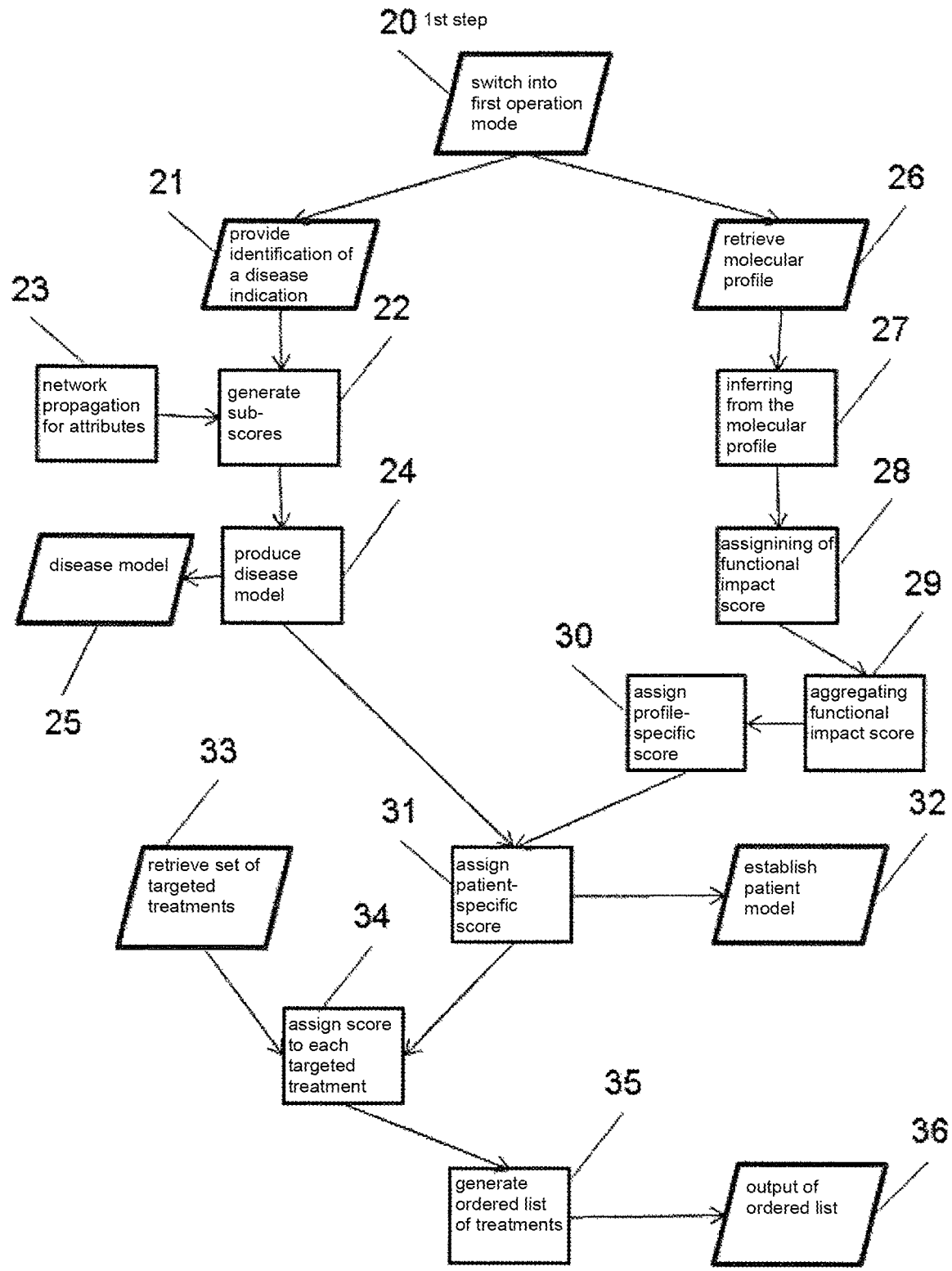
FIG. 2 is a flow diagram depicting a method for generating a personalized treatment guideline for a patient according to one implementation.

FIG. 2 shows a flow diagram depicting a method for generating a personalized treatment guideline for a patient according to one specific implementation.

In a first step 20, the processing unit 2 may be switched into the first operation mode as described with regard to FIG. 1. The first step 20 is optional, however, as the method may also start with retrieving an identification of a disease indication directly.

In step 21, an identification of a disease indication of the patient is provided to the processing unit 2. In some embodiments, the method involves a step 22, wherein sub-scores are generated from gene or protein attributes. Generating the sub-scores may further involve a step 23 of network propagation for gene or protein attributes which are considered with respect to related genes or proteins. In step 24, an indication-specific score is assigned to each gene or protein of a first set of genes or proteins as described with regard to FIG. 1. Step 24 produces a clinico-molecular disease model 25 representing several aspects of the involvement of genes and proteins into the disease, with may be outputted.

In step 26, a molecular profile of the patient is retrieved, as described with regard to FIG. 1.

In some embodiments, the method involves a step 27 of inferring from the molecular profile for each gene or protein of the first set of genes or proteins a possibly empty set of aberrations, a step 28 of assigning a functional impact score to each aberration and another step 29 of aggregating the functional impact score over the aberrations, as described with regard to FIG. 1.

In step 30, a profile-specific score is assigned to each gene or protein of the first set of genes or proteins, as described with regard to FIG. 1.

In step 31, a patient-specific score is assigned to each gene or protein of the first set of genes or proteins, the patient-specific score of each gene or protein combining its indication-specific score and its profile-specific score. With the patient-specific scores assigned to each gene or protein of the first set of genes or proteins, a patient model 32 is established and may be outputted.

In step 33, a set of targeted treatments, together with associated target proteins and/or the corresponding genes, is retrieved from a treatment database, as described with regard to FIG. 1.

In step 34, a score is assigned to each targeted treatment from the set of targeted treatments by aggregating the patient-specific scores at least over its associated target proteins and/or the corresponding genes.

In step 35, an ordered list of the targeted treatments is generated, wherein the order of the targeted treatments is determined by their score. The ordered list is outputted as the personalized treatment guideline 36.

Figure 3:
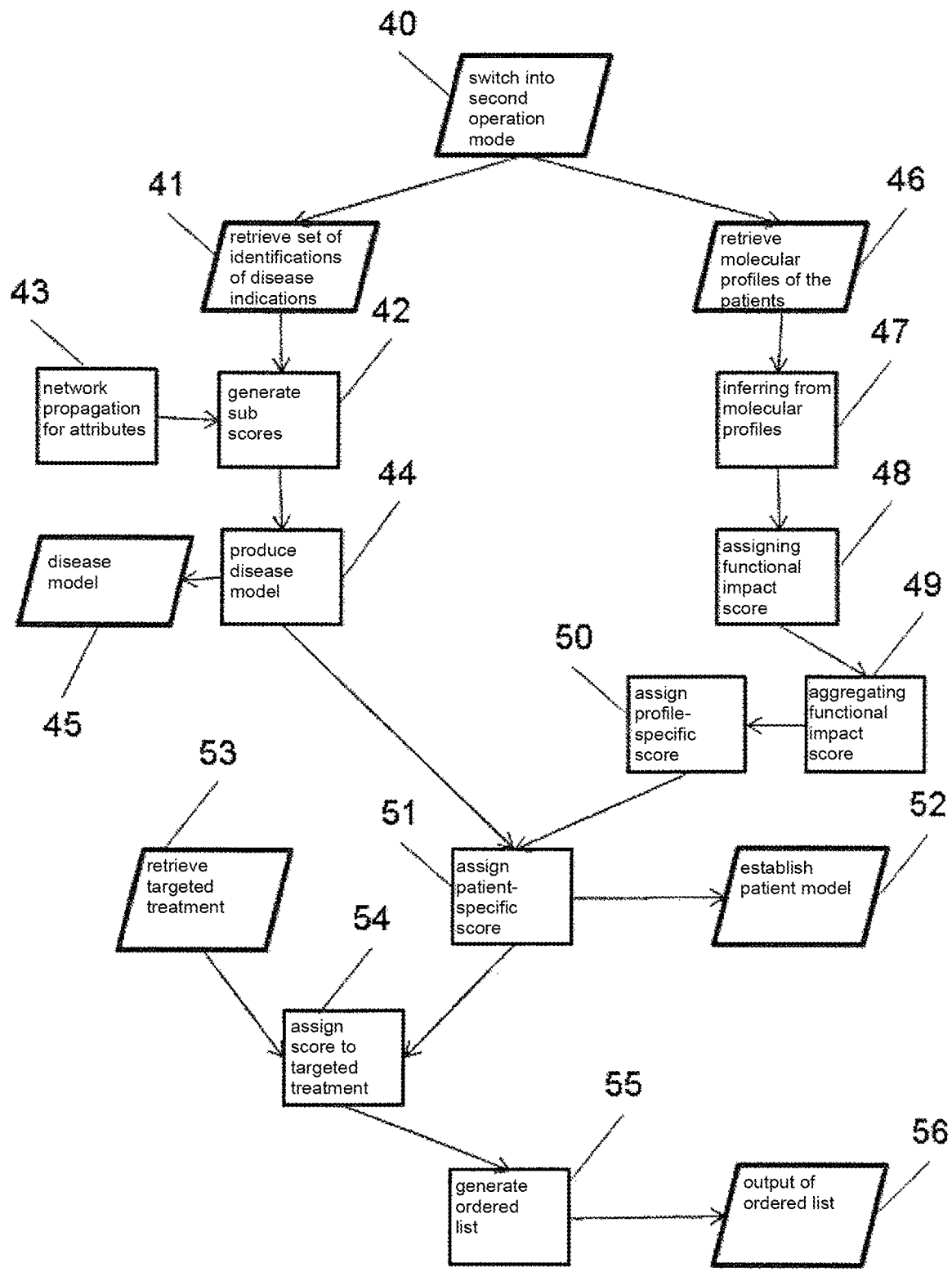
FIG. 3 shows an intermediate step for generating a personalized treatment guideline for a patient according to one implementation and FIG. 4 shows a directed graph with labeled nodes and edges, illustrating a part of a molecular interaction network and the corresponding computation of scores.

FIG. 3 shows a flow diagram depicting a method for selecting patients for a clinical trial of a treatment according to one implementation.

In a first step 40, the processing unit 2 may be switched into the second operation mode as described with regard to FIG. 1. The first step 40 is optional, however, as the method may also start with retrieving identifications of disease indications directly.

In step 41, a set of identifications of disease indications of patients is provided to the processing unit 2. In some embodiments, the method involves a step 42, wherein sub-scores are for each disease indication are generated from gene or protein attributes. Generating the sub-scores may further involve a step 43 of network propagation for gene or protein attributes which are considered with respect to related genes or proteins. In step 44, for every patient, an indication-specific score is assigned to each gene or protein of a first set of genes or proteins as described with regard to FIG. 1. Step 44 produces a clinico-molecular disease model 45 representing several aspects of the involvement of genes and proteins into the disease, with may be outputted.

In step 46, molecular profiles of the patients are retrieved, as described with regard to FIG. 1.

In some embodiments, the method involves, for every patient, a step 47 of inferring from the molecular profile for each gene or protein of the first set of genes or proteins a possibly empty set of aberrations, a step 48 of assigning a functional impact score to each aberration and another step 49 of aggregating the functional impact score over the aberrations, as described with regard to FIG. 1.

In step 50, for every patient, a profile-specific score is assigned to each gene or protein of the first set of genes or proteins, as described with regard to FIG. 1.

In step 51, for every patient, a patient-specific score is assigned to each gene or protein of the first set of genes or proteins, the patient-specific score of each gene or protein combining its indication-specific score and its profile-specific score. With the patient-specific scores assigned to each gene or protein of the first set of genes or proteins, a patient model 52 is established and may be outputted.

In step 53, for a targeted treatment associated target proteins and/or the corresponding genes are retrieved from a treatment database, as described with regard to FIG. 1.

In step 54, for every patient, a score is assigned to the targeted treatment from the set of targeted treatments by aggregating the patient-specific scores at least over its associated target proteins and/or the corresponding genes as described with regard to FIG. 1.

In step 55, an ordered list of the patients is generated, wherein the order of the targeted treatments is determined by their score. From the ordered list, patients may be selected for a clinical trial of the treatment and outputted.

Figure 4:
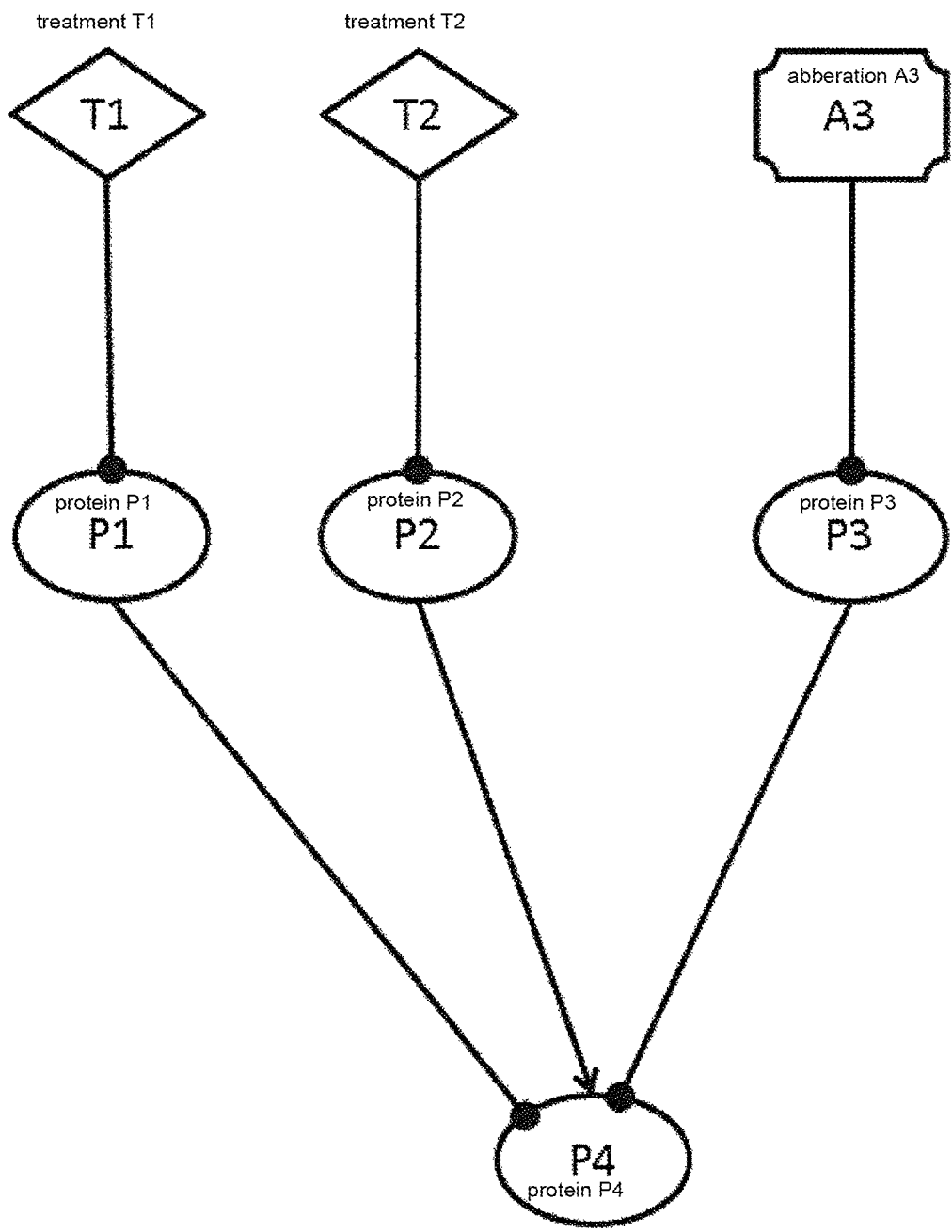

FIG. 4 shows a part of a molecular interaction network, represented as a directed graph with labeled nodes and edges. The three types of nodes are circles to represent proteins, diamonds to represent targeted drugs (hence treatments), and a square with clipped corners to represent an aberration. There are two types of edges, where an arrow represents activation, and a ball represents inhibition.

In this example, the indication-specific score shall be non-negative, which is the preferred embodiment. Specifically, let s1, s2, s3, and s4 denote the indication-specific scores of the proteins P1, P2, P3, and P4. Further, aggregations are performed by computing weighted sums with positive weights, which is the preferred embodiment.

Treatments T1 and T2 act by inhibiting their respective target proteins P1 and P2. The aberration A3 deactivates protein P3. P2 acts on P4 in such a way that increased or decreased activity of P2 cause changes in the activity of P4 in the same direction. P1 and P3 act on P4 in such a way that P4 reacts with a change in opposite direction to a change in the activity of P1 or P3.

The signed indirect functional impact scores of the proteins, determined by the aberration A3, are negative for P3 (as its function is inhibited by the aberration), positive for P4 (as its activity behaves reciprocally to that of P3), and zero for P1 and P2 (as they are not downstream of P3). Specifically, the inFIS may take the values (0,0,−1,+1) for the proteins (P1,P2,P3,P4).

The patient-specific score t1 for treatment T1 is computed by aggregating over its target proteins and the proteins downstream to its target proteins, which are P1 and P4 in this example. Hence t1=0*p1−(+1)*p4, which is a negative value.

The patient-specific score t2 for treatment T2 is computed by aggregating over its target proteins and the proteins downstream to its target proteins, which are P2 and P4 in this example. Hence t2=0*p2+(+1)*p4, which is a positive value.

As a result, treatment T2 is preferred over treatment T1: it will be placed higher in the ranked list of the patient-specific treatment guideline than T1. This corresponds to the fact that treatment with T1 has a similar effect on P4 as does the aberration A3, whereas treatment T2 has an effect of opposite directionality. Hence treating the patient with T2 has the potential of canceling part of the supposedly disease-causing effect of A3. Note that the degree of causal contribution to the disease is modeled and taken into account by the indication-specific scores.

EXAMPLES

TABLE 1

| Attribute | Indication | Subscore | Gene A |
|---|---|---|---|
| Cancer Biomarker | same | 10 | yes |
|  | related | 5 | yes |
|  | other | 3 | Yes |
| Cancer Drug Target | same | 10 | No |
|  | related | 5 | Yes |
|  | other | 3 | Yes |
| Oncogene | — | 8 | No |
| Suppressor | — | 5 | Yes |
| In core cancer pathway | — | 2 | Yes |

Table 1 shows details from step 22 described with regard to FIG. 2. Via table 1, an indication-specific score, in the specific case an Oncoscore, is calculated for an exemplary gene from the first set of genes or proteins. In table 1, the exemplary gene is indicated by "Gene A".

In table 1, gene or protein attributes are listed, here exemplarily "cancer biomarker", "cancer drug target", "oncogene", "suppressor" and "in core cancer pathway". Some of the attributes, here exemplarily "cancer biomarker" and "cancer drug target", involve further attributes. The further attributes exemplarily comprise information about the indication which the cancer biomarker or the cancer drug target is associated with. These further attributes are "same indication", "related indication", "other indication". The gene or protein attributes are associated with sub-scores, here exemplarily ranging from 2 to 10. The candidate gene "Gene A" is associated with the attributes per "yes" or "no".

Assigning the indication-specific score to the candidate gene may be performed by calculating a scalar product from the information about the candidate gene's attributes and the associated sub-scores. This results in if the candidate gene has the attribute, then its associated sub-score will be counted, otherwise not. In the example case, the oncoscore is 10+5+3+5+3+5+2=33.

While the invention is particularly shown and described with reference to specific embodiments, it should be understood by those skilled in the art that various changes in form and detail may be made therein.

The invention claimed is:

1. A method for generating a personalized treatment guideline for a patient, comprising:

retrieving an identification of a disease indication of the patient as a user's input, from an electronic health record or electronic medical record or from a patient database comprising medical records of a candidate set of patients;

assigning an indication-specific score to each gene or protein of a first set of genes or proteins, the first set of genes or proteins being part of the human genome or proteome, the indication-specific score reflecting an evidence of the gene or protein being associated with the disease indication of the patient, wherein the indication-specific score of each gene or protein is computed by first assigning numerical values to attributes indicating degrees of relationship to the indication and then by forming a weighted sum of the numerical values or of any monotonic transformation of the numerical values over the attributes, the attributes comprising at least one of the following list:

a) The gene or protein is a drug target,
b) The gene or protein is a biomarker or part of a biomarker,
c) The gene or protein is disease-associated,
d) The gene or protein is an oncogene or a product of an oncogene, respectively,
e) The gene or protein is a tumor suppressor,
f) The gene or protein has a cancer pathway association,
g) The gene or protein is gene ontology annotated for cancer relevant processes,
h) The gene or protein is part of a cancer-associated gene fusion,
i) The gene or protein has a tractable domain,
j) The gene or protein is embryonic lethal, and
k) The gene or protein is highly mutated in the specific indication;

retrieving a molecular profile of the patient, wherein the molecular profile comprises measurements of DNA or RNA extracted from the patient, produced by molecular measurement technology;

inferring, from the molecular profile, for each gene or protein of the first set of genes or proteins a possibly empty set of aberrations as the differences of the molecular profile to a reference profile from a control sample of the patient or from other individuals;

assigning a profile-specific score to each gene or protein of the first set of genes or proteins, the profile-specific score reflecting a degree of how much the function of the genes or proteins is altered by the aberrations, wherein assigning the profile-specific score to each gene or protein of the first set of genes or proteins comprises the following steps:

computing an aberration-specific functional impact score for each aberration, and computing a protein- or gene-specific direct functional impact score for each protein or gene by computing a weighted sum, a quantile, a median, a maximum or a geometric mean of the aberration-specific functional impact scores over the aberrations associated with the gene or protein, or computing a protein- or gene-specific indirect functional impact score for each protein or gene by computing a weighted sum, a quantile, a median, a maximum or a geometric mean of the aberration-specific functional impact scores over the aberrations associated with another set of genes or proteins, the another set including the gene or protein and a set of genes or proteins that are upstream of the gene or protein according to a molecular interaction network, the molecular interaction network being a directed graph, consisting of nodes each of which represents a gene or a protein, and of edges each of which connects two nodes, and wherein the profile-specific score is set equal to the direct functional impact score, equal to the indirect functional impact score or equal to a weighted sum of these;

assigning a patient-specific score to each gene or protein of the first set of genes or proteins, the patient-specific score of each gene or protein being a sum, a weighted sum, or a product of its indication-specific score and its profile-specific score;

retrieving a set of targeted treatments, together with associated target genes or proteins, as a user's input or by selecting treatments that are approved or under investigation for the indication of the patient or for related indications from a treatment database, the treatment database storing treatments, in particular drugs and drug combinations, together with information on the genes or proteins that are the targets of the drugs;

assigning a score to each targeted treatment from the set of targeted treatments by calculating a sum or a weighted sum over the patient-specific scores of the associated target genes or proteins;

generating the personalized treatment guideline as an ordered list of the targeted treatments, wherein the order of the targeted treatments is determined by their score; and administering of the selected treatment to the patient, wherein the treatment is selected based on the disease indication of the patient or a disease indication area of the patient or the first targeted treatment from the ordered list of the targeted treatments of the personalized treatment guideline is selected.

2. The method of claim 1, wherein the profile-specific score is set to zero if the gene or protein has no aberrations.

3. The method of claim 1, wherein assigning the score to a treatment comprises calculating an impact of the treatment on its associated target genes or proteins by adding the profile-specific scores of target genes or proteins that are inhibited or antagonized by the treatment and by subtracting the profile-specific scores of target genes or proteins that are activated or stimulated by the treatment.

4. The method of claim 1, wherein assigning the score to a treatment involves the step that patient-specific scores are further aggregated over genes or proteins downstream of their associated target genes or proteins according to the molecular interaction network by computing a weighted sum, a quantile, a median, a maximum or a geometric mean.

5. A system for generating a personalized treatment guideline for a patient, comprising:
one or more processors of a computing device in communication with a memory storing an electronic health record or electronic medical record or patient database comprising medical records of a candidate set of patients, the one or more processor configured to:
retrieve, from the electronic health record or electronic medical record or patient database, an identification of a disease indication of the patient;
assign an indication-specific score to each gene or protein of a first set of genes or proteins, the first set of genes or proteins being part of the human genome or proteome, the indication-specific score reflecting an evidence of the gene or protein being associated with the disease indication of the patient,
wherein the indication-specific score of each gene or protein is computed by first assigning numerical values to attributes indicating degrees of relationship to the indication and then by forming a weighted sum of the numerical values or of any monotonic transformation of the numerical values over the attributes, the attributes comprising at least one of the following list:
a) The gene or protein is a drug target,
b) The gene or protein is a biomarker or part of a biomarker,
c) The gene or protein is disease-associated,
d) The gene or protein is an oncogene or a product of an oncogene, respectively,
e) The gene or protein is a tumor suppressor,
f) The gene or protein has a cancer pathway association,
g) The gene or protein is gene ontology annotated for cancer relevant processes,
h) The gene or protein is part of a cancer-associated gene fusion,
i) The gene or protein has a tractable domain,
j) The gene or protein is embryonic lethal, and
k) The gene or protein is highly mutated in the specific indication;
retrieve a molecular profile of the patient, wherein the molecular profile comprises measurements of DNA or RNA extracted from the patient, produced by molecular measurement technology;
infer, from the molecular profile, for each gene or protein of the first set of genes or proteins a possibly empty set of aberrations as the differences of the molecular profile to a reference profile from a control sample of the patient or from other individuals;
assign a profile-specific score to each gene or protein of the first set of genes or proteins, the profile-specific score reflecting a degree of how much the function of the genes or proteins is altered by the aberrations,
wherein assigning the profile-specific score to each gene or protein of the first set of genes or proteins comprises the following steps:
computing an aberration-specific functional impact score for each aberration, and
computing a protein- or gene-specific direct functional impact score for each protein or gene by computing a weighted sum, a quantile, a median, a maximum or a geometric mean of the aberration-specific functional impact scores over the aberrations associated with the gene or protein, or
computing a protein- or gene-specific indirect functional impact score for each protein or gene by computing a weighted sum, a quantile, a median, a maximum or a geometric mean of the aberration-specific functional impact scores over the aberrations associated with another set of genes or proteins, the another set including the gene or protein and a set of genes or proteins that are upstream of the gene or protein according to a molecular interaction network, the molecular interaction network being a directed graph, consisting of nodes each of which represents a gene or a protein, and of edges each of which connects two nodes, and wherein the profile-specific score is set equal to the direct functional impact score, equal to the indirect functional impact score or equal to a weighted sum of these;

assign a patient-specific score to each gene or protein of the first set of genes or proteins, the patient-specific score of each gene or protein being a sum, a weighted sum, or a product of its indication-specific score and its profile-specific score;

retrieve a set of targeted treatments, together with associated target genes or proteins, as a user's input or by selecting treatments that are approved or under investigation for the indication of the patient or for related indications from a treatment database, the treatment database storing treatments, in particular drugs and drug combinations, together with information on the genes or proteins that are the targets of the drugs;

assign a score to each targeted treatment from the set of targeted treatments by calculating a sum or a weighted sum over the patient-specific scores of the associated target genes or proteins;

generate the personalized treatment guideline as an ordered list of the targeted treatments, wherein the order of the targeted treatments is determined by their score; and initiate administration of the selected treatment to the patient, wherein the treatment is selected based on the disease indication of the patient or a disease indication area of the patient or the first targeted treatment from the ordered list of the targeted treatments of the personalized treatment guideline is selected.

6. The system of claim 5, wherein the profile-specific score is set to zero if the gene or protein has no aberrations.

7. The system of claim 5, wherein assigning the score to a treatment comprises calculating an impact of the treatment on its associated target genes or proteins by adding the profile-specific scores of target genes or proteins that are inhibited or antagonized by the treatment and by subtracting the profile-specific scores of target genes or proteins that are activated or stimulated by the treatment.

8. The system of claim 5, wherein assigning the score to a treatment involves the step that patient-specific scores are further aggregated over genes or proteins downstream of their associated target genes or proteins according to the molecular interaction network by computing a weighted sum, a quantile, a median, a maximum or a geometric mean.

* * * * *